United States Patent
Cheon et al.

(10) Patent No.: US 11,766,664 B2
(45) Date of Patent: Sep. 26, 2023

(54) COBALT-BASED SINGLE-ATOM DEHYDROGENATION CATALYSTS HAVING IMPROVED THERMAL STABILITY AND METHOD FOR PRODUCING OLEFINS FROM CORRESPONDING PARAFFINS BY USING THE SAME

(71) Applicant: SK Innovation Co., Ltd., Seoul (KR)

(72) Inventors: Young Eun Cheon, Daejeon (KR); Hee Soo Kim, Daejeon (KR); Dong Min Yun, Daejeon (KR); Ho Won Lee, Daejeon (KR); Ju Hwan Im, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 17/358,230

(22) Filed: Jun. 25, 2021

(65) Prior Publication Data
US 2021/0402379 A1 Dec. 30, 2021

(30) Foreign Application Priority Data

Jun. 25, 2020 (KR) .................. 10-2020-0077570
Apr. 15, 2021 (KR) .................. 10-2021-0048929

(51) Int. Cl.
*B01J 23/75* (2006.01)
*B01J 37/08* (2006.01)
(Continued)

(52) U.S. Cl.
CPC ............... *B01J 23/75* (2013.01); *B01J 21/08* (2013.01); *B01J 35/0013* (2013.01);
(Continued)

(58) Field of Classification Search
CPC ........ B01J 23/75; B01J 21/08; B01J 35/0013; B01J 35/0046; B01J 35/023; B01J 35/026;
(Continued)

(56) References Cited

U.S. PATENT DOCUMENTS 5,347,046 A 9/1994 White et al.
5,453,558 A 9/1995 Alexander et al.
(Continued)

FOREIGN PATENT DOCUMENTS

CN 1123527 A 5/1996
CN 1151722 A 6/1997
(Continued)

OTHER PUBLICATIONS

Schweitzer et al., "Propylene Hydrogenation and Propane Dehydrogenation by a Single-Site Zn2+ on Silica Catalyst," ACS Catalysis, Feb. 21, 2014, pp. 1091-1098, vol. 4, American Chemical Society, Argonne, Illinois.
(Continued)

*Primary Examiner* — In Suk C Bullock
*Assistant Examiner* — Jason Y Chong
(74) *Attorney, Agent, or Firm* — THE WEBB LAW FIRM

(57) ABSTRACT

Disclosed herein are a dehydrogenation catalyst having single-atom cobalt loaded onto a silica support that has undergone pretreatment including a thermal treatment and a high-temperature aqueous treatment (reaction), a preparation method therefor, and a method for producing olefins by dehydrogenating corresponding paraffins, particularly light paraffins in the presence of the dehydrogenation catalyst.

17 Claims, 3 Drawing Sheets

(51) Int. Cl.
  *B01J 21/08* (2006.01)
  *B01J 35/00* (2006.01)
  *B01J 35/02* (2006.01)
  *B01J 37/02* (2006.01)
  *C07C 5/333* (2006.01)

(52) U.S. Cl.
  CPC ......... *B01J 35/0046* (2013.01); *B01J 35/026* (2013.01); *B01J 37/0217* (2013.01); *B01J 37/0221* (2013.01); *B01J 37/088* (2013.01); *C07C 5/3332* (2013.01); *C07C 2521/08* (2013.01); *C07C 2523/75* (2013.01)

(58) Field of Classification Search
  CPC .......... B01J 35/1019; B01J 35/1023; B01J 35/1042; B01J 37/009; B01J 37/0207; B01J 37/0209; B01J 37/0217; B01J 37/0221; B01J 37/06; B01J 37/08; B01J 37/088; B01J 37/10; B01J 37/14; C07C 5/3332; C07C 5/3335; C07C 2521/08; C07C 2523/75
  See application file for complete search history.

(56) References Cited

U.S. PATENT DOCUMENTS

| | | | |
|---|---|---|---|
| 5,475,144 A * | 12/1995 | Watson | ............. C07C 45/89 568/301 |
| 6,103,103 A | 8/2000 | Alexander et al. | |
| 6,733,657 B2 | 5/2004 | Benazzi et al. | |
| 10,040,054 B2 | 8/2018 | Rytter et al. | |
| 2012/0016171 A1 | 1/2012 | Kustov et al. | |
| 2013/0253248 A1 | 9/2013 | Gamoras et al. | |
| 2014/0128563 A1 | 5/2014 | McDaniel et al. | |
| 2014/0274672 A1 | 9/2014 | Kauffman et al. | |
| 2014/0275686 A1 * | 9/2014 | Hock | ............. B01J 23/72 502/259 |
| 2015/0141593 A1 | 5/2015 | Yang et al. | |
| 2016/0074838 A1 | 3/2016 | Hock et al. | |

FOREIGN PATENT DOCUMENTS

| | | |
|---|---|---|
| CN | 1151723 A | 6/1997 |
| CN | 101108362 A | 1/2008 |
| JP | 200829949 A | 2/2008 |
| JP | 2013505996 A | 2/2013 |
| JP | 2013511383 A | 4/2013 |
| KR | 100837195 B1 | 6/2008 |
| KR | 1020090116054 A | 11/2009 |
| KR | 1020180041794 A | 4/2018 |
| KR | 1020200049209 A | 5/2020 |
| KR | 1020210018566 A | 2/2021 |
| WO | 9633015 A1 | 10/1996 |
| WO | 2009136711 A2 | 11/2009 |

OTHER PUBLICATIONS

Keyvanloo et al., "Supported Iron Fischer-Tropsch Catalyst: Superior Activity and Stability Using a Thermally Stable Silica-Doped Alumina Support", American Chemical Society Catalysis, 2014, pp. 1071-1077, vol. 4.

Silica—Silicon Dioxide ($SiO_2$). Properties [online]. AZO Materials, 2001 [retrieved on Dec. 10, 2021]. Retrieved from the Internet: <URL: https://www.azom.com/properties.aspx?ArticleID=1114>.

Zhao et al., "Zirconium Modification Promotes Catalytic Activity of a Single-Site Cobalt Heterogeneous Catalyst for Propane Dehydrogenation" American Chemical Society Omega, 2018, pp. 11117-11127, vol. 3.

Zirconia—$ZrO_2$, Zirconium Dioxide. Properties [online], AZO Materials, 2001 [retrieved on Dec. 10, 2021], Retrieved from the Internet: <URL: https://www.azom.com/properties.aspx?ArticleID=133>.

Notice of Allowance issued in KR 2021-0048929 dated Dec. 5, 2022. (English Translation).

Goldsmith et al., "Beyond Ordered Materials: Understanding Catalytic Sites on Amorphous Solids", ACS Catalysis, 2017, pp. 7543-7557, vol. 7.

Jimenez et al., "Influence of coordination environment of anchored single-site cobalt catalyst $CO_2$ hydrogenation", ChemCatChem, 2019, pp. 1-10.

* cited by examiner

COBALT-BASED SINGLE-ATOM DEHYDROGENATION CATALYSTS HAVING IMPROVED THERMAL STABILITY AND METHOD FOR PRODUCING OLEFINS FROM CORRESPONDING PARAFFINS BY USING THE SAME

CROSS-REFERENCE TO RELATED APPLICATIONS

This application claims priority to Korean Patent Application Nos. 10-2020-0077570 filed Jun. 25, 2020 and 10-2021-0048929 filed Apr. 15, 2021, the disclosures of which are hereby incorporated by reference in their entirety.

BACKGROUND OF THE INVENTION

1. Field of the Invention

The present disclosure relates to a cobalt-based single-atom dehydrogenation catalyst having improved thermal stability and a method for producing olefins from corresponding paraffins by using the same. More particularly, the present disclosure relates to a dehydrogenation catalyst having single-atom cobalt loaded onto a silica support that has undergone pretreatment including a thermal treatment and a high-temperature aqueous treatment (reaction), a preparation method therefor, and a method for producing olefins by dehydrogenating corresponding paraffins, particularly light paraffins in the presence of the dehydrogenation catalyst.

2. Description of the Prior Art

Recently, attention have been paid to catalyst techniques of loading active metals to supports and utilizing the same. Particularly, with the advance of nanotechnologies, active studies on loading nano-sized active metals to supports are ongoing. Although having excellent activity compared to that of conventional catalysts, nano-sized active metals, when used as catalysts, suffer from the disadvantages of causing side reactions or undergoing rapid deactivation due to their broad size distribution and irregular morphologies.

Meanwhile, a catalyst having metal loaded in a single atom size can maximize catalytic activity by downsizing metal active sites to a sub-nano size atomic level. Specifically, due to their extremely simple and ideal structures, single-atom catalysts are advantageous in simulating theoretical results obtained through computational science, etc. to conduct relevant studies. In this regard, catalysts in which transition metals such as zinc (Zn) and cobalt (Co) are loaded in the form of single atom on supports (e.g., silica) and have been used for dehydrogenation of light paraffins.

In addition, it has been reported that when supported, single-atom active metals enjoy the advantage of minimizing cracking and suppressing formation of cokes during catalytic reactions (e.g., ACS Catal. 2014, 4, 4, 1091-1098). However, the prior art techniques have shortcomings from the commercial viewpoint because a mixed gas (containing 3% of propane and the balance of the inert gas argon (Ar) as reactants) is used to maintain a low concentration of reactants in selectively converting paraffins to the corresponding olefins while suppressing the formation of by-products, and reactions are conducted at low temperatures in order to prolong catalyst life spans.

Moreover, when the dehydrogenation of paraffins in the presence of a catalyst having single-atom cobalt as an active metal loaded on a support is conducted at high temperatures, the aggregation (or agglomeration) of the cobalt elements immobilized on the support or the formation of elemental cobalt attributed to a reduction phenomenon occurs, thus making it difficult to secure long-term reaction stability or durability.

Suggested in order to overcome the problems described above was a method in which an alkali metal is introduced to a support, thereby reducing the aggregation of active cobalt metals on the support (Korean Patent Publication No. 2020-0049209 A). However, there is a still problem that continuous exposure to a high temperature upon dehydrogenation induces a shrinking behavior of the support and thus aggregates the active metal, decreasing stability of the catalyst. In addition, the alkali metal introduced upon catalyst preparation drastically reduces the volume of the silica support during dehydrogenation, giving rise to the aggregation of metal ions or sintering due to the reduction of surface area. Furthermore, the use of alkali metals in loading single-atom active metals requires expensive complicated processes for the synthesis, thus making it difficult to prepare single-atom catalysts on a commercial scale. Therefore, there is a need for a catalyst preparation method that is convenient and by which active metals are prevented from aggregating over a long period of time and can stably retain a single-atom form.

SUMMARY OF THE INVENTION

An embodiment according to the present disclosure provides a single-atom cobalt (Co)-loaded catalyst that exhibits improved catalytic stability or long-term activity even upon exposure to a high temperature as in the production of olefins through dehydrogenation of paraffins, and a preparation method therefor.

Another embodiment according to the present disclosure provides a dehydrogenation process which is desirable in terms of conversion of paraffins even for feedstocks containing a high concentration of paraffins, and selectivity for corresponding olefins and is thus suitable for commercialization.

Provided according to a first aspect of the present disclosure is a method for preparation of a single-atom cobalt-based catalyst, which comprises the steps of:

a) thermally treating silica as a support at a temperature ranging from 600 to 870° C. to induce shrinkage of the support, and simultaneously to remove its surface hydroxyl groups, followed by subjecting the shrunken support to a high-temperature aqueous reaction to afford a pretreated silica having hydroxyl groups selectively activated thereon;

b) preparing an aqueous dispersion of the pretreated silica;

c) preparing a pH-adjusted aqueous dispersion of the pretreated silica by adding a base to the aqueous dispersion of the pretreated silica to adjust the pH of the dispersion to at least 10;

d) separately, preparing a pH-adjusted cobalt precursor aqueous solution by preparing an aqueous solution of a cobalt precursor having an oxidation number of 3+ and adding a base to the aqueous solution;

e) combining the pH-adjusted aqueous dispersion of the pretreated silica with the pH-adjusted aqueous solution of the cobalt precursor to afford an aqueous dispersion in which at least a part of the cobalt ions having an oxidation number of 3+ is adsorbed onto the surface of the pretreated silica;

f) removing cobalt ions which remain not adsorbed onto the pretreated silica; and g) thermally treating the cobalt ion-adsorbed silica obtained in step f);

wherein the cobalt having an oxidation number of 2+ exists in an isolated form of single-atom on the pretreated silica while being tetrahedrally coordinated at the trihydroxyl groups present on the surface of the pretreated silica.

Provided according to a second aspect of the present disclosure is a method for production of olefins from paraffins, the method comprising the steps of:

providing a feedstock containing light paraffins;

subjecting the feedstock to dehydrogenation at a temperature of 500 to 700° C. under a pressure of 0.3 to 2 bar in the presence of the catalyst prepared according to the method; and recovering the olefins corresponding to the light paraffin from the dehydrogenation product.

The dehydrogenation catalyst according to an embodiment of the present disclosure has cobalt loaded in a single-atom form on a silica support pretreated by conducting thermal (heat) treatment and subsequent selective activation of hydroxyl groups, and can guarantee thermal durability to the support without introduction of additional metal even upon exposure to high temperatures (e.g., about 500° C. or higher) during dehydrogenation of paraffins, especially light paraffins to corresponding olefins, whereby the shrinkage (or contraction) of the support itself and the shrinkage-induced aggregation or sintering of cobalt on the support surface can be effectively suppressed. Therefore, even when exposed to high temperatures for a long period of time during dehydrogenation or being in contact with the hydrogen generated by the dehydrogenation, the catalyst is effectively protected from deformation or degeneration and thus retain the long-term catalytic activity.

For prior art silica-based cobalt metal catalysts intended to secure thermal stability by introducing alkali metal thereto, the silica support rapidly decreases in volume during dehydrogenation due to the alkali metal introduced to the silica. The reduction of surface area in turn causes the metal ions to aggregate or undergo sintering, imparting a limitation to the long-term catalytic activity. In an embodiment of the present disclosure, however, the pre-treatment including thermal treatment and selective activation of hydroxyl groups (high-temperature aqueous treatment), instead of the introduction of alkali metal ions, can suppress the volumetric shrinkage of the silica support itself. Further, despite the loss of hydroxyl groups by the thermal treatment, the selective activation of hydroxyl groups reassembles the surface active groups that can effectively support active metal ions. In addition, the catalysts according to some embodiments of the present disclosure exhibit high conversion and selectivity for olefins when performing dehydrogenation even on a feedstock containing a high concentration of paraffins and thus are particularly advantageous for commercialization.

BRIEF DESCRIPTION OF THE DRAWINGS

The above and other aspects, features and advantages of the present disclosure will be more apparent from the following detailed description taken in conjunction with the accompanying drawings, in which.

DESCRIPTION OF THE INVENTION

Figure 1:
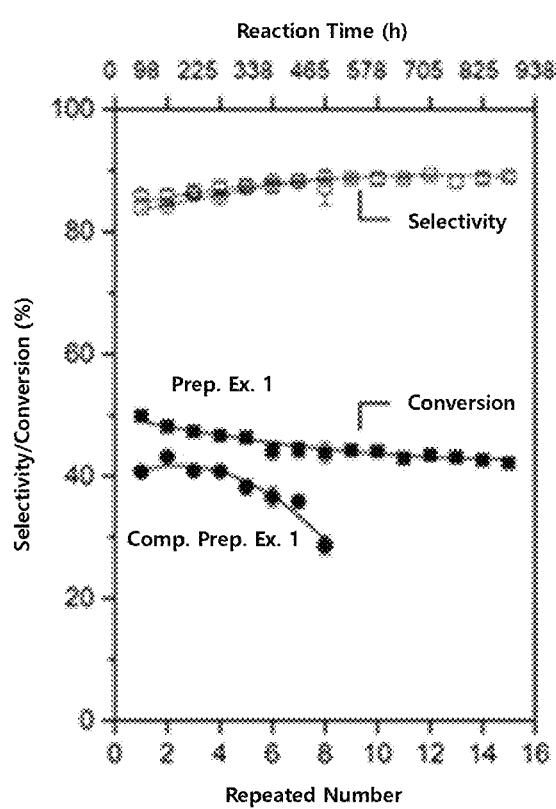
FIG. 1 is a graph showing conversion and selectivity when carrying out dehydrogenation in the presence of each of the cobalt-based single-atom catalysts prepared using a pretreated silica support (Preparation Example 1) and a non-pretreated silica support (Comparative Preparation Example 1) with time.

The present disclosure can be all accomplished by the following description. It is to be understood that the following description illustrates preferable embodiments of the present disclosure, but the present disclosure is not necessarily limited thereto. It is also to be understood that the accompanying drawings are included to provide a further understanding of the present disclosure and are not intended to limit the scope of the present disclosure.

The terms used herein are defined as follows.

As used herein, the term "heterogeneous catalyst" refers to a catalyst that is present in a different phase from a reactant in a catalyst reaction process. By way of example, a heterogeneous catalyst may remain undissolved in a reaction medium. When a heterogeneous catalyst is used, the onset of a reaction occurs with the diffusion and adsorption of reactants onto the surface of the heterogeneous catalyst. After completion of the reaction, a product needs to be desorbed from the surface of the heterogeneous catalyst.

The term "support", as used herein, refers to a material (typically a solid-phase material) with a high specific surface area, to which a catalytically active component is attached, and the support may or may not be involved in a catalytic reaction.

As used herein, the term "crystalline" refers typically to any solid substance in which atoms are arranged to have a lattice structure (e.g., a three-dimensional order) while the term "amorphous" refers to any solid substance that does not have such a lattice structure. The substances may each be identified by X-ray diffraction (XRD), nuclear magnetic resonance (NMR), differential scanning calorimetry (DSC), or a combination thereof.

As used herein, the term "light paraffin" refers to a paraffin of 2 to 5 carbon atoms, more particularly, a paraffin of 3 or 4 carbon atoms, as exemplified by ethane, propane, n-butane, isobutane, and pentane. In addition, "corresponding olefin" refers to an olefin resulting from the removal of a hydrogen molecule from a light paraffin in a feedstock by dehydrogenation and thus having the same number of carbon atoms as the paraffin.

The term "silica", as used herein, refers to a substance of tetrahedral coordination in which four oxygen atoms bind to one silicon atom.

As used herein, the term "porous silica" refers to a three-dimensional network silica having porosity, which may be composed of an aggregate of primary silica particles.

As used herein, the term "heat treatment" or "thermal treatment" refers to an intentional temperature increase in the entirety or part of a subject, optionally with the entailment of additional chemical or physical treatment so as to achieve a desired specific structure and physical property (or change).

The expression "does not substantially comprise" is intended to not incorporate a specific ingredient, but can be construed to allow the ingredient to be incorporated in an impurity form.

Throughout the description, the terms "on" and "over" are used to refer to the relative positioning, and mean not only that one component or layer is directly disposed on another component or layer but also that one component or layer is indirectly disposed on another component or layer with a further component or layer (intermediate layer) being interposed therebetween. Likewise, spatially relative terms, such as "below", "beneath", "lower", and "between", may be used herein for ease of description to refer to the relative positioning. Also, the term "sequentially" may be understood as a relative positioning concept.

Whenever a numerical range is indicated herein, it is meant to include any cited numeral within the indicated range and any sub-combination with any two values within the range set forth as a lower limit and an upper limit. For example, "1 to 5" is understood to include 1, 2, 3, 4, and 5, and any sub-combination within the range.

Throughout the description, unless explicitly described to the contrary, the word "comprise" and variations such as "comprises" or "comprising" will be understood to imply the inclusion of stated elements and/or steps, but not the exclusion of any other elements.

An embodiment of the present disclosure provides a cobalt-based single-atom catalyst and particularly a heterogenous catalyst having single-atom cobalt as an active metal loaded onto a silica support, wherein the catalyst is suitable not only for converting a feedstock containing a high concentration of paraffins (particularly, light paraffins) to corresponding olefins with high conversion and selectivity, but also exhibits notable thermal stability even upon exposure to high temperatures during dehydrogenation.

For a cobalt-based, single-atom catalyst according to an embodiment, the selective activation of hydroxyl groups on the silica, particularly, the silica support can not only load the active metal single-atom cobalt onto the support, without additionally or separately introducing heterogenous metal (e.g., alkali metal) thereinto, but also suppresses volumetric shrinkage during dehydrogenation, whereby the silica can be used as a support guaranteeing thermal durability and long-term activity.

Pretreatment of Silica Support

According to an embodiment, pretreatment including thermal treatment and high-temperature aqueous treatment (activation of hydroxyl groups) may be performed on silica (initial silica) in order to confer the above-described properties on the silica support.

In an exemplary embodiment, the initial silica provided prior to the pretreatment step is not limited to particular types, but may advantageously employ high-purity silica that is as low in impurity content as possible. According to a specific embodiment, such initial silica may be amorphous silica, particularly porous amorphous silica, including for example, fumed silica (dry silica), precipitated silica (wet silica), or the like.

In an exemplary embodiment, the initial silica (silica prior to pretreatment) may be in a particulate form with a particle size (diameter) of, for example, about 0.5 to 5000 μm, particularly about 10 to 1000 μm, and more particularly about 400 to 800 μm. However, the particle size ranges described above should be understood to be illustrative.

According to an exemplary embodiment, the initial silica has a specific surface area (BET specific area) of, for example, at least about 100 m$^2$/g, particularly about 200 to 1500 m$^2$/g, and more particularly about 300 to 1000 m$^2$/g. The initial silica may range in pore volume, for example, from about 0.1 to 10 cm$^3$/g, particularly from about 0.3 to 5 cm$^3$/g, and more particularly from about 0.5 to 3 cm$^3$/g and in pore size (average diameter), for example, from about 0.5 to 200 nm, particularly from about 1 to 100 nm, and more particularly from about 3 to 30 nm. It, however, should be understood that the numerical ranges are given for illustrative purposes.

In an exemplary embodiment, the initial silica may have a surface hydroxyl concentration (or content) of, for example, about 3 to 5 mmol/cc, particularly about 3.2 to 4.8 mmol/cc, and more particularly about 3.5 to 4.5 mmol/cc.

According to an embodiment, thermal treatment (a first thermal treatment) in the pretreatment is conducted to reduce the volume of the initial silica. This thermal treatment can prevent the vulnerability to high temperatures of the silica, for example, amorphous silica, used as a support in conventional cobalt single-atom catalysts.

According to an embodiment, the initial silica is thermally treated or sintered at a high temperature, for example, about 600 to 870° C., particularly about 650 to 850° C., and more particularly about 700 to 800° C. In this regard, too low a thermal treatment temperature makes it difficult to induce desired volumetric shrinkage. In contrast, when the thermal treatment is conducted at too a high temperature, excessive shrinkage occurs, making it difficult to recover (or activate) hydroxyl groups at a subsequent step (high-temperature aqueous treatment). Hence, it is advantageous to establish the thermal treatment in the range described above.

According to an exemplary embodiment, the thermal treatment of silica may be conducted for, for example, about 3 to 12 hours, particularly about 4 to 11 hours, and more particularly about 5 to 10 hours. In addition, the thermal treatment may be carried out in an oxygen-containing atmosphere, for example, in an air atmosphere. During the thermal treatment, a temperature elevation rate may be adjusted within a range of, for example, about 1 to 20° C./min, particularly about 2 to 10° C./min, and more particularly about 4 to 7° C./min, which are, however, understood to be illustrative.

During the thermal treatment described above, the silica, particularly, the amorphous silica is crystallized upon exposure to the high temperature, during which water molecules are removed therefrom and volumetric shrinkage occurs. By way of example, the volume of the thermally treated silica may be reduced (i.e., shrunken) by about 75% or less, particularly about 5 to 70%, more particularly about 10 to 60%, and even more particularly about 20 to 50%, compared to the pre-treatment (initial) silica.

However, the thermal treatment converts substantially all the hydroxyl groups on the surface of silica (particularly, amorphous silica) as well as inside the silica into silicon oxide, thus removing even hydroxyl functional groups that is capable of immobilizing the active metal cobalt thereto. In detail, the surface of the thermally treated silica loses hydroxyl groups thereof due to the high temperature and thus does not allow electrostatic interaction through which the cobalt precursor can be effectively adsorbed or immobilized to the surface of the silica support. As such, the preliminary (or preceding) thermal treatment performed for the silica support during the catalyst preparation can suppress the dehydrogenation-induced volumetric shrinkage of the catalyst to some degree, while weakening the function of loading the active metal cobalt in a single-atom form. For instance, the silica may have the surface hydroxyl group concentration less than about 0.2 mmol/cc, particularly less than about 1.5 mmol/cc, more particularly less than about 1 mmol/cc.

Taking this circumstance into consideration, high-temperature aqueous treatment (reaction) is performed in order to selectively activate surface hydroxyl groups (i.e., hydroxylation function) on the silica that has undergone the thermal treatment-induced volumetric shrinkage (or contraction). The high-temperature aqueous treatment forms free hydroxyl groups on the surface of the silica, thus enabling the effective adsorption or immobilization of cobalt metal ions as described below. Without being bound by particular theory, the reasons for the high-temperature aqueous treatment can be explained as follows.

On the surface of the typical silica (initial silica), hydroxyl groups bound by hydrogen bonds and free hydroxyl groups coexist. However, after the removal of hydroxyl groups from the silica surface via the aforementioned thermal treatment, the high-temperature aqueous treatment activates hydroxyl groups, generating a great deal of free hydroxyl groups on the silica surface. The free hydroxyl groups thus formed can immobilize cobalt ions and are suitable for forming a tetrahedral structure of trihydroxyl groups with a cobalt atom.

In addition, free hydroxyl groups present on the surface of initial silica become close to each other as the support is contracted upon exposure to a high temperature, and thus the subsequently loaded cobalt ions may aggregate. However, the combined thermal treatment and the high-temperature aqueous treatment prevent the shrinkage of the silica support, thus enabling the free hydroxyl groups to keep the cobalt ions a certain distance apart from each other. Moreover, the thermal treatment conducted prior to the high-temperature aqueous treatment can attain additional thermal stability because the weak hydroxyl group bound by hydrogen bonds as well as the preexisting free hydroxyl group on the silica surface are removed thereby.

According to an exemplary embodiment, the silica support can be provided with the immobilization capability of cobalt ion amounting to at least about 0.8% by weight, particularly at least about 1% by weight, more particularly 1 to 2% by weight, and even more particularly about 1.2 to 1.5% by weight, based on the weight of the pretreated silica support, by virtue of the free hydroxyl groups formed through the pretreatment (particularly high-temperature aqueous treatment).

In an exemplary embodiment, the high-temperature aqueous treatment may be conducted by dispersing the thermally treated silica in an aqueous medium to give a silica-aqueous dispersion and then boiling the dispersion at, for example, about 70 to 150° C., particularly about 90 to 130° C., more particularly about 95 to 110° C. for about 0.5 to 12 hours, particularly about 1 to 10 hours, or more particularly about 3 to 8 hours.

In this regard, the aqueous medium for use in forming a dispersion of the high-temperature aqueous treated (or reacted) silica (e.g., thermally treated silica) may be water, particularly distilled water. The content of silica in the thermally treated silica-aqueous dispersion may range, for example, from about 1 to 30% by weight, particularly from about 3 to 20% by weight, and more particularly from about 5 to 10% by weight.

After the high-temperature aqueous treatment, the thermally treated silica may increase in volume (i.e., volume expansion). By way of example, the high-temperature aqueous treatment may increase the volume of the thermally treated silica by about 5 to 50%, particularly about 10 to 30%, and more particularly about 15 to 25%. In addition, the silica particles may have a size of, for example, about 0.3 to 4000 μm, particularly about 5 to 900 μm, and more particularly about 300 to 700 μm after the high-temperature aqueous treatment. However, the particle sizes of the high-temperature aqueous treated silica vary depending on the initial size, and thus are understood to be illustrative.

According to an exemplary embodiment, the hydroxyl groups formed by the high-temperature aqueous treatment (that is, activated hydroxyl groups) are higher in thermal durability than those present on the surface of initial silica, and allow the stable maintenance of the tetrahedral structure of trihydroxyl groups which immobilizes cobalt thereto, thus effectively inhibiting the aggregation of the active metal single-atom cobalt during the dehydrogenation. Moreover, the increased stability of the tetrahedral structure decreases the influence of the hydrogen generated during the reaction and increases the resistance of cobalt to reduction, thereby preventing the activity from rapidly decreasing during the dehydrogenation. According to an exemplary embodiment, the concentration (content or amount) of the surface hydroxyl groups, which is reduced by the thermal treatment, can be recovered to the initial level by the high-temperature aqueous treatment, and may range from about 3 to 5 mmol/cc, particularly from about 3.2 to 4.8 mmol/cc, and more particularly from about 3.5 to 4.5 mmol/cc, which are however understood to be illustrative.

Without being bound by any particular theory, the high-temperature aqueous treatment (reaction) can recover the total amount (concentration) of hydroxyl groups on the silica surface to a level similar to that of the initial state, and secures thermal stability in the silica to prevent the silica support from contracting. In addition, the free hydroxyl groups suitable for immobilizing (fixing) single atom-type cobalt ions exist in a high proportion while the hydroxyl groups improper for immobilizing single atom-type cobalt ions, such as the hydroxyl groups bound by hydrogen bonds, decrease quantitatively.

In an embodiment, the silica that has undergone the pretreatment is characterized by a decrease in at least one of specific surface area, pore volume, and pore size. This is because once a remarkable decrease in volume (i.e., shrinkage) is induced by the thermal treatment, the silica cannot be completely restored to its initial state (before the pretreatment) even though the high-temperature aqueous treatment is conducted for selective activation after the thermal treatment.

After the high-temperature aqueous treatment, the pretreated silica is separated from the dispersion by using any typical separation and/or purification techniques (for example, at least one selected from filtration, settling (or stagnation), washing, etc.) and can be used as a support for depositing cobalt thereon. Alternatively, the aqueous dispersion of the pretreated silica may be used, as it is, for supporting cobalt without the aforementioned separation and/or purification steps.

Loading of Single-Atom Cobalt on Pretreated Silica Support

According to an embodiment, the pretreated silica is dispersed in an aqueous medium to give pretreated silica-containing aqueous dispersion. In this regard, the aqueous medium may be water, particularly, distilled water, as described above. In addition, the content of the pretreated silica in the pretreated silica-containing aqueous dispersion may be in the range of, for example, about 1 to 30% by weight, particularly about 3 to 20% by weight, and more particularly about 5 to 10% by weight.

Next, a base is added to the pretreated silica-containing aqueous dispersion to prepare a pH-adjusted pretreated silica aqueous dispersion. The pH of the aqueous dispersion may be adjusted into, for example, at least about 10, particularly at least about 11, and more particularly about 10.5 to 11.5.

The reason of increasing the pH of the dispersion is to deprotonate the silica surface. Specifically, hydrogen ions ($H^+$) are removed from the silanol (Si—OH) present on the surface of the pretreated silica (that is, protons are removed from hydroxyl groups) to impart a negative charge. That is, since ions are not adsorbed at the point of zero charge of silica and hydroxyl groups are maintained, the silica surface is negatively charged by deprotonation through pH adjustment.

As a result, the deprotonated, negatively charged hydroxyl ions on the silica surface and the hydroxyl groups present on the silica surface, specifically the trihydroxyl groups, form three hydroxyl anions in an basic (or alkaline) aqueous medium, providing sites to which cobalt is immobilized (fixed) or grafted in a single-atom form through electrostatic interaction (i.e., electrostatic adsorption) in the subsequent step (i.e., selective activation of hydroxyl groups). Such immobilization mechanism distinguishes from a passive manner in which alkali metals are interposed between cobalt ions to provide sites for immobilizing cobalt ions in a single-atom form thereto. Particularly, it is noticeable that the accelerated shrinkage phenomenon of the silica support itself, which is attributable to the use of alkali metal, is effectively prevented during the dehydrogenation.

According to an exemplary embodiment, the base ingredient may be at least one selected from, for example, sodium hydroxide, potassium hydroxide, ammonium hydroxide, and the like. The base ingredient may be particularly an ammonium-containing base ingredient and more particularly ammonium hydroxide (ammonia water). Advantageously, the base should not cause precipitation in the subsequent step, e.g., when combined or mixed with an aqueous solution of the cobalt precursor.

According to an embodiment of the present disclosure, separately from the preparation step of the pH-adjusted aqueous dispersion of the pretreated silica, a step of preparing an aqueous solution of a cobalt precursor and adding a base to the aqueous solution may be conducted to prepare a pH-adjusted cobalt precursor aqueous solution.

In this regard, the cobalt precursor may include a cobalt (Co(III)) complex ion having an oxidation number of 3+. For example, $Co(NH_3)_6Cl_3$ may be directly used or at least one cobalt compound (precursor) selected from $Co(NO_3)_2$, $CoCl_2$, and $Co(acac)_3$ is treated with ammonia water and filtered to obtain a precursor including a cobalt complex ion. The employment of $Co(NH_3)_6Cl_3$ may be advantageous for easygoing formation of a cobalt single-atom catalyst because it can minimize the preparation steps.

In an exemplary embodiment, the precursor aqueous solution may contain a cobalt precursor at a concentration of, for example, about 0.1 to 20% by weight, particularly about 0.5 to 10% by weight, and more particularly about 1 to 5% by weight.

Moreover, the pH of the cobalt precursor solution can be adjusted with a base (an alkaline ingredient). The pH adjustment enables the silica surface to stably retain a deprotonated state (that is, modified to have a negative charge) upon combination or contact with the pH-adjusted aqueous dispersion of the pretreated silica in the subsequent step, whereby the positively charged cobalt ions ($Co^{3+}$) of the precursor can be fixed or attached to the silica surface through electrostatic adsorption. In this regard, the base may be at least one selected from those used for the preparation of the pretreated silica aqueous dispersion. By way of example, the base or basic compounds used in each of the preparation steps may be the same. According to circumstances, different base may be employed. Even in this case, the base that does not cause precipitation when mixed with an aqueous solution of the cobalt precursor is desirable. In an exemplary embodiment, the addition of a base can adjust the pH of the aqueous cobalt precursor solution to, for example, at least about 10, particularly at least about 11, and more particularly about 10.5 to 11.5.

After the pH-adjusted aqueous solution of the Co(III) precursor is prepared as described above, a step of combining the pH-adjusted aqueous solution of the Co(III) precursor with the pH-adjusted aqueous dispersion of the pretreated silica. The mixing ratio between the pH-adjusted aqueous solution of the cobalt precursor and the pH-adjusted aqueous dispersion of the pretreated silica may be determined considering the amount in which the cobalt ions in the aqueous cobalt precursor solution can be fixed in a form of single-atom (particularly single-atom of a single layer) on the surface of the pretreated silica. In this regard, cobalt ions may be loaded in the form of single atom by at most about 2% to 3% by weight onto the surface of the pretreated silica. However, all of the cobalt precursor used cannot be fixed onto the surface of the pretreated silica in practice. Thus, an excess of a cobalt (Co(III)) precursor larger than the theoretical amount may be dissolved. In an exemplary embodiment, the mixing ratio between the pH-adjusted aqueous solution of the cobalt precursor and the pH-adjusted aqueous dispersion of the pretreated silica may be adjusted so that the amount of the cobalt precursor may be at least about 1% by weight, particularly about 1 to 20% by weight, more particularly about 2 to 10% by weight, and even more particularly about 3 to 8% by weight, based on the weight of the pretreated silica.

According to an exemplary embodiment, the combination of the two aqueous fluids (i.e., the aqueous silica-dispersion and aqueous cobalt precursor solution) may be carried out under stirring. The stirring may be conducted at a speed of, for example, about 200 to 500 rpm, and particularly about 250 to 400 rpm and may be continued, for example, for at least about 3 minutes, particularly at least about 5 minutes, and more particularly about 5 to 10 minutes, without limitations thereto. A temperature for the mixing or combination may be set to be, for example, about 10 to 40° C., particularly about 20 to 30° C., and more particularly room temperature, without limitations thereto.

Then, cobalt remaining unfixed in a single-atom form onto the surface of the silica surface is removed as much as possible from the aqueous dispersion of the cobalt precursor-adsorbed silica. This process, which makes the method of the present disclosure different from a conventional impregnation method, is to leave only cobalt (or $Co^{3+}$) that is fixed in single-atom forms onto the silica surface by electrical interaction while eliminating the others. As in the conventional impregnation method, for example, a cobalt precursor attached in a bulk state onto a silica surface induces reduction, aggregation, etc., which lowers catalytic activity during the dehydrogenation.

In full consideration of the foregoing, the solids (cobalt precursor-adsorbed (fixed), pretreated silica) in the combined dispersion can be separated from the liquid by settling, filtration, etc., and as necessary, the separated solids may be subjected to repeated cycles of adding water, particularly distilled water, stirring, and separating. In addition, the separated solids may be washed with water, particularly distilled water at least once, particularly two or more times to remove as much the cobalt precursor remaining unattached as possible. Next, the solids thus obtained may be dried at a temperature of, for example, about 10 to 40° C., particularly about 20 to 30° C., and more particularly at room temperature, but without limitation thereto. At this time, the cobalt ions still retain an oxidation number of +3.

In a subsequent step, the cobalt-adsorbed (immobilized) silica is converted to a dehydrogenation catalyst by thermal treatment (a second thermal treatment). This thermal treatment may be conducted in an oxygen-containing atmosphere (i.e., calcination), at, for example, about 250 to 1000° C., particularly about 270 to 800° C., more particularly about 280 to 600° C., and even more particularly about 290 to 400° C. In the present embodiment, when the cobalt-adsorbed (fixed) silica is thermally treated, the cobalt adsorbed onto the silica changes in oxidation number from 3+ to 2+. In addition, the temperature elevation rate in the thermal treatment may be controlled in the range of, for example, about 1 to 20° C./min, particularly about 1.5 to 10° C./min, and more particularly 2 to 7° C./min.

Optionally, an additional drying step may be conducted prior to the thermal treatment in an oxygen-containing atmosphere. In this regard, the temperature in the additional drying step may range, for example, from about 50 to 150° C. and particularly from about 120 to 150° C. In the course of such a relatively high-temperature drying, at least a part of the cobalt atoms having an oxidation number of 3+ may be partially reduced to cobalt atoms having an oxidation number of 2+ in advance. Then, the remaining cobalt atoms may be converted into an oxidation number of 2+ during the thermal treatment.

Without being bound by a particular theory, the reason why the cobalt retains an oxidation number of 2+ after the thermal treatment is explained as follows.

For cobalt with an oxidation number of 3+, only the octahedral structure is possible because six electrons occupy the outmost orbital to enable the formation of six bonds. When the cobalt is reduced to 2+, seven electrons exist in the outmost orbital, thus mainly forming a tetrahedral structure, while an octahedral structure is also possible as in CoO. According to the present embodiment, it is supposed that the cobalt is reduced to 2+ to form a tetrahedral structure because it should structurally bind to the trihydroxyl groups. On the other hand, in order to return back to 3+, the cobalt should form an octahedron in cooperation with its surroundings. At this time, silicon (Si) does not have any structure other than a tetrahedron in nature, which is in discord with the octahedral structure of cobalt, and thus making it difficult to convert the reduced cobalt to the oxidized state 3+. In contrast, the deactivation arises when the linkage (communication) to Si is cleaved to cause Co metal to aggregate alone. Accordingly, it is considered that the formation of an oxide by contact with oxygen could result in $Co_3O_4$ containing cobalt of the oxidation state 3+.

In addition, so long as it guarantees the conversion of the oxidation number of cobalt from 3+ to 2+, any time could be set for the heat treatment and may be, for example, about 2 to 12 hours, particularly about 2.5 to 8 hours, and more particularly about 3 to 4 hours, but are not particularly limited thereto.

The cobalt with the oxidation number 2+, converted by heating at a predetermined temperature or higher during the thermal treatment, is not returned back to the oxidation number 3+ even though the thermal treatment is continued in an oxygen-containing (or oxidation) atmosphere (or calcining atmosphere). The reason is because the single-atom cobalt needs to retain a tetrahedral structure. Furthermore, even when the catalyst is applied to the dehydrogenation conducted at a predetermined temperature or higher, the oxidation state remains unchanged, implying that the catalyst according to the present embodiment is resistant to reduction.

According to an embodiment, the cobalt ions with an oxidation number of 2+ may be coupled in the form of isolated single atoms with the negatively charged $SiO^-$ on the surface of the pretreated silica by electrostatic interaction or adsorption. As such, the single-atom cobalt is tetrahedrally coordinated at the trihydroxyl (or three hydroxyl) groups present on the silica surface. By way of example, such trihydroxyl groups may come from or be in the form of trihydroxyl ring or tridentated hydroxyl ring.

The thermal treatment and high-temperature aqueous treatment conducted for the silica support prior to the immobilization of cobalt has advantages over the conventional techniques employing alkali metals, as follows:

Introduction of alkali metal intended to compensate for or secure thermal durability rather promotes volumetric shrinkage or contraction, resulting in reducing the volume of silica support itself by about 30% or more during the reaction. In contrast, possible volumetric shrinkage is preliminarily induced by conducting thermal treatment prior to the immobilization of the active metal, i.e., cobalt (Co) in a single-atom form in an embodiment of the present disclosure, whereby the silica support can be prevented from undergoing the volumetric shrinkage caused during the dehydrogenation.

In addition, although it is allowable that the catalyst inevitably contains alkali metal in a trace amount (for example, less than about 0.001% by weight, based on the weight of the catalyst), the introduction of alkali metal to offer a loading site for cobalt as in the conventional preparation methods of cobalt single-atom catalysts may be excluded. In this context, the dehydrogenation catalyst according to a particular embodiment is substantially free of alkali metal.

Therefore, the cobalt single-atom catalyst according to an embodiment can prevent the volumetric shrinkage-induced cobalt aggregation, without introduction of additional metal ions thereto, and can keep the cobalt ions in the form of isolated single atoms with the introduction of a great number of free hydroxyl groups having thermal durability thereinto. As a result, the dehydrogenation catalyst retains its own activity and long-term durability.

According to an exemplary embodiment, the content (loading amount) of cobalt in the dehydrogenation catalyst may be, for example, at least about 1% by weight, particularly about 1.1 to 3% by weight, and more particularly about 1.2 to 2% by weight. The loading amount may somewhat vary depending on kinds of the silica, but may be determined considering that the maximum amount of the cobalt present in a single atom form is typically in the range of about 2 to 3% by weight.

Dehydrogenation

According to another embodiment thereof, the present disclosure provides a process of converting a paraffin, particularly light paraffin (more particularly light paraffin of 2 to 5 carbon atoms), to the corresponding olefin by using the aforementioned cobalt-based, single-atom catalyst. Particularly, the light paraffin may contain propane. In this regard, a feedstock may be provided as a gas phase.

When applied even to a feedstock containing a high content of paraffins, the catalyst can achieve better conversion and selectivity. By way of example, the content of paraffins in a feedstock may be, for example, at least about 50% by volume, particularly at least about 70% by volume, more particularly at least about 80% by volume, and higher than about 99% by volume. This differs from the experimental results in which a feedstock containing paraffins at most about 20% by volume is subjected to dehydrogenation in the presence of the conventional single-atom catalyst (e.g., Zn catalyst).

In the dehydrogenation according to an exemplary embodiment, the reaction temperature may range, for example, from about 500 to 700° C., particularly from about 550 to 650° C., and more particularly from about 570 to 620° C. In addition, a pressure of, for example, about 0.3 to 2 bar, particularly about 0.4 to 1.5 bar, and more particularly about 0.5 to 1 bar may be set for the dehydrogenation. As for the gas hourly space velocity (GHSV), its range may be chosen to be, for example, about 100 to 2000 $hr^{-1}$, particularly about 200 to 1500 $hr^{-1}$, and more particularly about 300 to 1000 $hr^{-1}$ in a standard condition. The dehydrogenation conditions may vary depending on kinds of paraffins in the feedstock, active metals in the catalyst, the loading amounts and ratios of alkali metals, etc.

According to an exemplary embodiment, the conversion and selectivity in the dehydrogenation may be, for example, at least about 30% (particularly at least about 40%), and at least about 70% (particularly at least about 80%), respectively.

A better understanding of the present disclosure may be obtained through the following examples which are set forth to illustrate, but are not to be construed as limiting the present disclosure.

EXAMPLES

Analysis instrument and methods used in the Examples are as follows.

EXAFS

In order to investigate the single-atom cobalt in the cobalt single-atom catalyst and to analyze surroundings around the single-atom cobalt, Co K-edge (7.709 keV) X-ray absorption spectroscopy (XAFS) was measured and recorded at the 8C beamline (nano-XAFS (X-ray absorption spectroscopy), 4-20 keV, $10^{12}$ photons/sec) of the Pohang Light Source (PAL PLS-II). The gas was controlled to set the absorption rates of $I_0$ and It+Ir at 15% and 85%, respectively. The monochromator was detuned to 70%. All the specimens except for a reference (0.1 mm) were each powdered, loaded to a 2 mm slit, and made planar before measurement in a transmission mode. The wavelet transformation was accomplished by the HAMA-Fortran program using Morlet mother wavelet in the range of k=2-11 $Å^{-1}$ and R=1-4 Å, with η=8 and σ=1.

Calculation of Conversion and Selectivity

Conversion and selectivity of propane were calculated according to Equations 1 and 2, below.

$$\text{Conversion Rate of propane (\%)} = \frac{\text{Weight of propane in reactant} - \text{Weight of unconverted propane in product}}{\text{Weight of propane in reactant}} \times 100 \quad [\text{Equation 1}]$$

$$\text{Selectivity for propylene (\%)} = \frac{\text{Weight of propylene in product}}{\text{Weight of propane in reactant} - \text{Weight of unconverted propane in product}} \times 100 \quad [\text{Equation 2}]$$

Preparation Example 1

Among commercially available silica (tradename Q6 from Fuji), particles having an average size of 500 μm or greater, a specific surface area of 450 $m^2/g$ or greater, and a pore volume of 0.8 $cm^3/g$ or greater were selected, thermally treated at 850° C. for 6 hours in an air atmosphere, and then cooled to obtain thermally treated silica. Next, 10 g of the thermally treated silica was dispersed in 100 mL of distilled water, boiled at 100° C. for 2 hours, cooled, and filtered to obtain pretreated silica particles. Hereinafter, the silica that has undergone the thermal treatment and the high-temperature aqueous treatment is referred to as "post-pretreated silica".

After the pretreatment, a dispersion of 10 g of the post-pretreated silica in 100 mL of distilled water was prepared and added with 28% by weight of ammonia water (Sigma-Aldrich) to afford a pH-adjusted aqueous dispersion of the post-pretreated silica having a pH of 11.

In a separate beaker, 0.5 g of the cobalt precursor (Co$(NH_3)_6Cl_3$) was dissolved in 50 mL of distilled water. The aqueous cobalt precursor solution was controlled to have a pH of 11 by adding 28% by weight of ammonia water (Sigma-Aldrich) thereto.

Subsequently, the pH-adjusted, aqueous cobalt precursor solution was added to the pH-adjusted aqueous dispersion of the post-pretreated silica, followed by stirring at room temperature for 1 hour. The stirred dispersion was filtered and then washed several times with distilled water.

The filtrate was dried at room temperature and then at 120° C. for 6 hours, heated to 300° C. at a rate of 2° C./min, and thermally treated for 2 hours at the temperature in an air atmosphere to prepare a dehydrogenation catalyst.

Comparative Preparation Example 1

Among commercially available silica (tradename Q6 from Fuji), particles having an average size of 500 μm or greater were selected. Next, 10 g of the silica was dispersed in 100 mL of distilled water. To the dispersion, 28% by weight of ammonia water (Sigma-Aldrich) was added to afford a pH-adjusted aqueous dispersion of the post-pretreated silica having a pH of 11.

In a separate beaker, 0.5 g of the cobalt precursor (Co$(NH_3)_6Cl_3$) was dissolved in 50 mL of distilled water. The aqueous cobalt precursor solution was controlled to have a pH of 11 by adding 28% by weight of ammonia water (Sigma-Aldrich) thereto.

Subsequently, the pH-adjusted, aqueous cobalt precursor solution was added to the pH-adjusted aqueous dispersion of silica, followed by stirring at room temperature for 1 hour. The stirred dispersion was filtered and then washed several times with distilled water.

The filtrate was dried at room temperature and then at 120° C. for 6 hours, heated to 300° C. at a rate of 2° C./min, and thermally treated for 2 hours at the temperature in an air atmosphere to prepare a dehydrogenation catalyst.

Preparation Example 2

Among commercially available silica (tradename Q6 from Fuji), particles having an average size of 500 μm or greater, a specific surface area of 450 $m^2/g$ or greater, and a pore volume of 0.8 $cm^3/g$ or greater were selected, thermally treated at 600° C. for 6 hours, and then cooled to obtain thermally treated silica. Next, 10 g of the thermally treated silica was dispersed in 100 mL of distilled water, boiled at 100° C. for 2 hours, cooled, and filtered to obtain silica particles. Hereinafter, the silica that has undergone the thermal treatment and the high-temperature aqueous treatment is referred to as "post-pretreated silica".

A dispersion of 10 g of the post-pretreated silica in 100 mL of distilled water was prepared and added with 28% by weight of ammonia water (Sigma-Aldrich) to afford a pH-adjusted aqueous dispersion of the post-pretreated silica having a pH of 11.

In a separate beaker, 0.5 g of the cobalt precursor (Co(NH$_3$)$_6$Cl$_3$) was dissolved in 50 mL of distilled water. The aqueous cobalt precursor solution was controlled to have a pH of 11 by adding 28% by weight of ammonia water (Sigma-Aldrich) thereto.

Subsequently, the pH-adjusted, aqueous cobalt precursor solution was added to the pH-adjusted aqueous dispersion of the post-pretreated silica, followed by stirring at room temperature for 1 hour. The stirred dispersion was filtered and then washed several times with distilled water.

The filtrate was dried at room temperature and then at 120° C. for 6 hours, heated to 300° C. at a rate of 2° C./min, and thermally treated for 2 hours at the temperature in an air atmosphere to prepare a dehydrogenation catalyst.

Preparation Example 3

Among commercially available silica (tradename Q6 from Fuji), particles having an average size of 500 μm or greater, a specific surface area of 450 m$^2$/g or greater, and a pore volume of 0.8 cm$^3$/g or greater were selected, thermally treated at 700° C. for 6 hours in an air atmosphere, and then cooled to obtain thermally treated silica. Next, 10 g of the thermally treated silica was dispersed in 100 mL of distilled water, boiled at 100° C. for 2 hours, cooled, and filtered to obtain pretreated silica particles. Hereinafter, the silica that has undergone the thermal treatment and the high-temperature aqueous treatment is referred to as "post-pretreated silica".

A dispersion of 10 g of the post-pretreated silica in 100 mL of distilled water was prepared and added with 28% by weight of ammonia water (Sigma-Aldrich) to afford a pH-adjusted aqueous dispersion of the post-pretreated silica having a pH of 11.

In a separate beaker, 0.5 g of the cobalt precursor (Co(NH$_3$)$_6$Cl$_3$) was dissolved in 50 mL of distilled water. The aqueous cobalt precursor solution was controlled to have a pH of 11 by adding 28% by weight of ammonia water (Sigma-Aldrich) thereto.

Subsequently, the pH-adjusted, aqueous cobalt precursor solution was added to the pH-adjusted aqueous dispersion of the post-pretreated silica, followed by stirring at room temperature for 1 hour. The stirred dispersion was filtered and then washed several times with distilled water.

The filtrate was dried at room temperature and then at 120° C. for 6 hours, heated to 300° C. at a rate of 2° C./min, and thermally treated for 2 hours at the temperature in an air atmosphere to prepare a dehydrogenation catalyst.

Preparation Example 4

Among commercially available silica (tradename Q6 from Fuji), particles having an average size of 500 μm or greater, a specific surface area of 450 m$^2$/g or greater, and a pore volume of 0.8 cm$^3$/g or greater were selected, thermally treated at 800° C. for 6 hours in an air atmosphere, and then cooled to obtain thermally treated silica. Next, 10 g of the thermally treated silica was dispersed in 100 mL of distilled water, boiled at 100° C. for 2 hours, cooled, and filtered to obtain pretreated silica particles. Hereinafter, the silica that has undergone the thermal treatment and the high-temperature aqueous treatment is referred to as "post-pretreated silica".

A dispersion of 10 g of the post-pretreated silica in 100 mL of distilled water was prepared and added with 28% by weight of ammonia water (Sigma-Aldrich) to afford a pH-adjusted aqueous dispersion of the post-pretreated silica having a pH of 11.

In a separate beaker, 0.5 g of the cobalt precursor (Co(NH$_3$)$_6$Cl$_3$) was dissolved in 50 mL of distilled water. The aqueous cobalt precursor solution was controlled to have a pH of 11 by adding 28% by weight of ammonia water (Sigma-Aldrich) thereto.

Subsequently, the pH-adjusted, aqueous cobalt precursor solution was added to the pH-adjusted aqueous dispersion of the post-pretreated silica, followed by stirring at room temperature for 1 hour. The stirred dispersion was filtered and then washed several times with distilled water.

The filtrate was dried at room temperature and then at 120° C. for 6 hours, heated to 300° C. at a rate of 2° C./min, and thermally treated for 2 hours at the temperature in an air atmosphere to prepare a dehydrogenation catalyst.

Comparative Preparation Example 2

Among commercially available silica (tradename Q6 from Fuji), particles having an average size of 500 μm or greater, a specific surface area of 450 m$^2$/g or greater, and a pore volume of 0.8 cm$^3$/g or greater were selected, thermally treated at 900° C. for 6 hours in an air atmosphere, and then cooled to obtain thermally treated silica. Next, 10 g of the thermally treated silica was dispersed in 100 mL of distilled water, boiled at 100° C. for 2 hours, cooled, and filtered to obtain pretreated silica particles. Hereinafter, the silica that has undergone the thermal treatment and the high-temperature aqueous treatment is referred to as "post-pretreated silica".

A dispersion of 10 g of the post-pretreated silica in 100 mL of distilled water was prepared and added with 28% by weight of ammonia water (Sigma-Aldrich) to afford a pH-adjusted aqueous dispersion of the post-pretreated silica having a pH of 11.

In a separate beaker, 0.5 g of the cobalt precursor (Co(NH$_3$)$_6$Cl$_3$) was dissolved in 50 mL of distilled water. The aqueous cobalt precursor solution was controlled to have a pH of 11 by adding 28% by weight of ammonia water (Sigma-Aldrich) thereto.

Subsequently, the pH-adjusted, aqueous cobalt precursor solution was added to the pH-adjusted aqueous dispersion of the post-pretreated silica, followed by stirring at room temperature for 1 hour. The stirred dispersion was filtered and then washed several times with distilled water.

The filtrate was dried at room temperature and then at 120° C. for 6 hours, heated to 300° C. at a rate of 2° C./min, and thermally treated for 2 hours at the temperature in an air atmosphere to prepare a dehydrogenation catalyst.

Contents of cobalt in the catalysts prepared according to Preparation Examples 1 to 3 and Comparative Preparation Examples 1 and 2 are summarized in Table 1, below.

TABLE 1

| | Preparation Example No. | | | | | |
|---|---|---|---|---|---|---|
| | C. 1 | 2 | 3 | 4 | 1 | C. 2 |
| Co Content (% by weight) | 1.2 | 1.1 | 1.1 | 1.5 | 1.3 | 0.7 |

As is understood from the results of Preparation Examples 1 to 4 and Comparative Preparation Example 2 in Table 1, the loading amount of cobalt was affected by the temperature of thermal treatment in the pretreatment step. In Comparative Example 2, the excessively high temperature of thermal treatment led to insufficient activation of the hydroxyl groups, which results in limiting a proper loading amount of cobalt in a single-atom form even though the high-temperature aqueous treatment was conducted after the thermal treatment.

Experimental Example 1

In this experiment, a reactant gas containing a high content of paraffins was subjected to dehydrogenation in the presence of each cobalt-loaded catalyst prepared in Preparation Examples 1 to 4 and Comparative Preparation Examples 1 and 2 to synthesize olefins.

The dehydrogenation for catalyst evaluation was carried out using a ¾-inch quartz tube reactor (¾ inches for diameter in the catalyst loading region and ¼ inch for diameter for the other tube region). Flow rates of the gas were controlled using a mass flow controller, and the product gas from the reactor was analyzed using an online gas chromatography apparatus (50 m HP-PLOT column).

Of the catalysts, 6 cc (about 3 g) was weighed and loaded by quartz wool in the reaction tube through which $N_2$ was then allowed to flow at a flow rate of 100 cc/min while the temperature was elevated from room temperature to 590° C. at a rate of 5° C./min.

For dehydrogenating paraffin, the reactant gas containing 99.5% propane (regas) was introduced at a flow rate of 20 cc/min into the reactor. The composition of the gas from the reactor was analyzed using FID (flame ionization detector).

Conversion and Selectivity Evaluation

When applied to dehydrogenation, the cobalt-based single-atom catalyst prepared using a pretreated silica support (Preparation Example 1) and the cobalt-based single-atom catalyst prepared using a non-pretreated silica support (Comparative Preparation Example 1) were analyzed in terms of conversion and selectivity with time. The results are depicted in FIG. 1.

As is understood from the results of dehydrogenation in the figure, the catalyst of Preparation Example 1 was similar in selectivity, but superior in conversion to that of Comparative Preparation Example 1. These results indicate that equivalent or higher yields can be obtained from the catalyst of Preparation Example 1, compared to that of Comparative Preparation Example 1.

SEM Analysis

Figure 2:
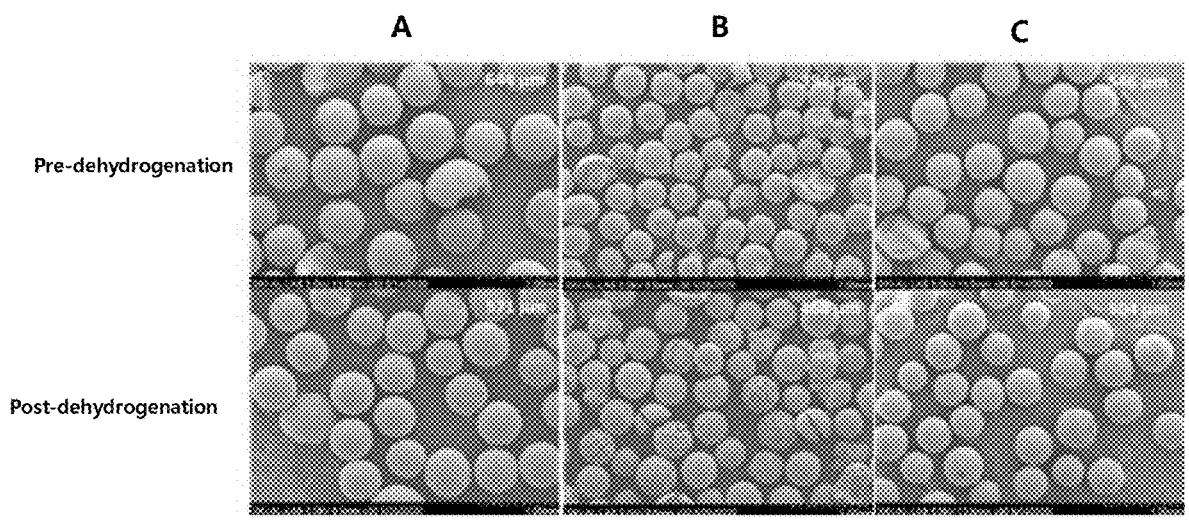
FIG. 2 shows SEM images of cobalt single-atom catalysts using, as supports, non-pretreated silica particles, silica particles undergoing thermal (heat) treatment only, and silica particles undergoing thermal (heat) treatment-hydroxyl group activation, respectively, before and after dehydrogenation.

Shown in FIG. 2 are SEM images taken of Co single-atom catalysts having, as supports, non-pretreated silica particles (A), silica particles that have undergone thermal treatment-hydroxyl group activation (C) before and after dehydrogenation reactions, together with silica particles that have undergone thermal treatment only (B).

As shown in the images, the Co single-atom catalyst having non-pretreated silica as the support thereof (A) reduced in particle size by 10% or more due to the shrinkage of the silica support during the dehydrogenation. In addition, the Co single-atom catalyst in which silica undergoing only thermal treatment is used as a support (B) shrank in volume by 40%, compared to the Co single-atom catalyst having non-pretreated silica as a support. The preliminarily reduced volume of the catalyst did not increase or decrease significantly after dehydrogenation. However, it is observed that the catalyst was partially damaged during dehydrogenation as cracks were generated on the surface of the catalyst.

In contrast, the Co single-atom catalyst having, as the support thereof, the silica that has undergone thermal treatment and then high-temperature aqueous treatment (hydroxyl group activation) (C) increased in particle size by 20%, compared to the Co single-atom catalyst that has undergone thermal treatment only, but was observed to remain almost unchanged in size before and after dehydrogenation and not experience the particle damages attributed to the dehydrogenation temperature.

Taken together, the experimental results obtained in the foregoing indicate that whereas the Co catalyst having non-pretreated silica as a catalyst support reduces in volume due to the heat during dehydrogenation, the preliminary thermal treatment on silica during the pretreatment can prevent the volumetric shrinkage of the catalyst support during dehydrogenation. In addition, the high-temperature aqueous treatment (hydroxyl group activation) compensates for the thermal treatment-induced loss of hydroxyl groups on the silica surface which provokes a decreased load of the active metal in the catalyst, whereby the silica support can exhibit increased resistance to volumetric shrinkage and can load an optimal amount of the active metal thereon, leading to the fabrication of a catalyst excellent in thermal durability.

EXAFS Wavelet Transform Analysis

Figure 3:
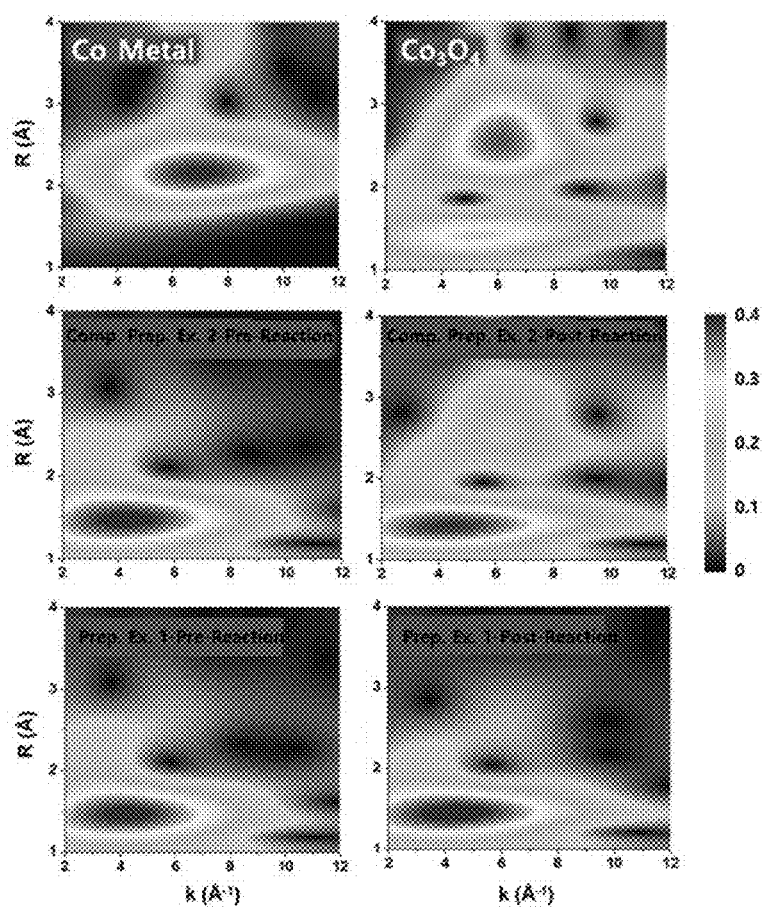
FIG. 3 shows EXAFS Wavelet Transform analysis results of cobalt single-atom catalysts before and after dehydrogenation.

The cobalt-based catalysts prepared according to Preparation Example 1 and Comparative Preparation Example 2 were analyzed for EXAFS Wavelet Transform and the spectra are given in FIG. 3.

As can be seen in the spectra, Co metal exhibited a single pattern at R=2.2 Å, which is characteristic of the Co—Co bond, accounting for the presence of Co metal.

For the typical Co oxide $Co_3O_4$, two patterns were observed: first pattern for Co—O (R=1.5 Å) and second pattern for Co—O—Co (R=2.5 Å). In this regard, a bulky oxide has repeats of unit lattice structures. Typically, the pattern intensities at high R values are greater than the first pattern intensity because the numbers (8 and 12) of the second most adjacent atoms are greater than those (4 and 6) of the most adjacent atoms. That is, the oxides in the particles form crystals where unit cell structures are repeated, accounting for the development of the second pattern. Therefore, the spectra in which the second pattern is well developed indicate the existence of cobalt oxides.

In this context, the cobalt single-atom catalyst is characterized by the highly intense pattern only at the low R value (R=1.5 Å).

Referring to FIG. 3, the two cobalt catalysts (before reaction) prepared according to Preparation Example 1 and Comparative Preparation Example 2 both showed well developed first patterns, but second patterns were not identified in either of them, indicating that Co atoms are away from each other, with no structure developed therebetween. These analysis results imply that the Co catalysts in both of the samples exist in single-atom forms before the reaction.

Experimental Example 2

In this experiment, multiple rounds of dehydrogenation were conducted for producing olefins from reactant gas containing a high content of paraffins in the presence of the cobalt-based catalysts prepared according to Preparation Example 1 and Comparative Preparation Example 2.

Briefly, dehydrogenation was performed using the same instrument under the initial reaction conditions as in Experimental Example 1. For the initial dehydrogenation, the reactant gas containing 99.5% propane (regas) was introduced at a flow rate of 20 cc/min into the reactor and maintained for 1 hour. After one hour of the dehydrogenation, the reaction tube was purged by flowing $N_2$ gas at a flow rate of 100 cc/min for 30 min. The composition of the gas from the reactor was automatically sampled at regular intervals of 15 min before analysis with FID (flame ionization detector). In a regeneration step of the catalyst, air (99.999%) was allowed to flow at a flow rate of 100 cc/min to eliminate cokes generated in the reaction step, after which the reaction tube was purged by flowing $N_2$ gas at a flow rate of 10 cc/min for 30 min.

The four steps of reaction-purge-regeneration-purge, as described above, were repeated five times before the catalyst changes were analyzed by EXAFS. The results are depicted in FIG. 3.

As shown in the figure showing catalyst analysis results after dehydrogenation with the catalysts of Preparation Example 1 and Comparative Preparation Example 2, the catalyst of Preparation Example 1 exhibited almost the same patterns as before dehydrogenation while the second pattern (R=2.5 Å) in the catalyst of Comparative Preparation Example 2 was strongly developed, compared to that before dehydrogenation, indicating the conversion of the Co single-atom form to an oxide form during the dehydrogenation. Therefore, the catalyst of Preparation Example 1 maintains Co single-atom states before and after the reaction whereas the catalyst of Comparative Preparation Example 2 differs in Co state before and after the reaction.

Accordingly, it should be understood that simple modifications and variations of the present disclosure may be easily used by those skilled in the art, and such modifications or variations may fall within the scope of the present disclosure.

What is claimed is:

1. A method for preparation of a single-atom cobalt-based catalyst, which comprises the steps of:
   a) thermally treating silica as a support at a temperature ranging from 600 to 870° C. to induce shrinkage of the support, and simultaneously to remove its surface hydroxyl groups, followed by subjecting the shrunken support to a high-temperature aqueous treatment in a temperature range of 70 to 150° C. to afford a pretreated silica having hydroxyl groups selectively activated thereon;
   b) preparing an aqueous dispersion of the pretreated silica;
   c) preparing a pH-adjusted aqueous dispersion of the pretreated silica by adding a base to the aqueous dispersion of the pretreated silica to adjust the pH of the dispersion to at least 10;
   d) separately preparing a pH-adjusted cobalt precursor aqueous solution by preparing an aqueous solution of a cobalt precursor having an oxidation number of 3+ and adding a base to the aqueous solution;
   e) combining the pH-adjusted aqueous dispersion of the pretreated silica with the pH-adjusted aqueous solution of the cobalt precursor to afford an aqueous dispersion in which at least a part of the cobalt ions having an oxidation number of 3+ is adsorbed onto the surface of the pretreated silica;
   f) removing cobalt ions which remain not adsorbed onto the pretreated silica; and
   g) thermally treating the cobalt ion-adsorbed silica obtained in step f);
   wherein cobalt having an oxidation number of 2+ exists in an isolated form of single-atom on the pretreated silica while being tetrahedrally coordinated at trihydroxyl groups present on the surface of the pretreated silica.

2. The method of claim 1, wherein the thermally treated silica in step a) reduces in volume by 75% compared to the silica before the pretreatment, and the silica after the high-temperature aqueous treatment increases in volume by 5 to 50%, compared to the thermally treated silica.

3. The method of claim 1, wherein the silica before the pretreatment of step a) is amorphous silica.

4. The method of claim 3, wherein the silica before the pretreatment in step a) is in a particle form with a particle size of 0.5 to 5000 μm.

5. The method of claim 1, wherein the silica in step a) contains hydroxyl groups at a concentration of 3 to 5 mmol/cc on the surface thereof before the thermal treatment and at a concentration of less than 0.2 mmol/cc on the surface thereof after the thermal treatment, and at a concentration of 3 to 5 mmol/cc on the surface thereof after the high-temperature aqueous treatment.

6. The method of claim 1, wherein the pretreated silica has a cobalt ion immobilization capability of at least about 0.8% by weight.

7. The method of claim 1, wherein the high-temperature aqueous treatment in step a) is conducted by the steps of:
   dispersing the thermally treated silica in an aqueous medium to give a thermally treated silica-aqueous dispersion; and
   boiling the thermally treated silica-aqueous dispersion at 70 to 150° C.

8. The method of claim 7, wherein the thermally treated silica-aqueous dispersion contains silica at a content of 1 to 30% by weight.

9. The method of claim 1, wherein the pretreated silica obtained in step a) ranges in particle size from 0.3 to 4000 μm.

10. The method of claim 1, wherein the pretreated silica-containing aqueous dispersion prepared in step b) ranges in concentration from 1 to 30% by weight.

11. The method of claim 1, wherein the base used in steps c) and d) are same or different and are each at least one selected from the group consisting of sodium hydroxide, potassium hydroxide, and ammonium hydroxide.

12. The method of claim 1, wherein the cobalt precursor in step d) contains a cobalt complex ion having an oxidation number of 3+(Co(III)), and the aqueous solution of a cobalt precursor contains the cobalt precursor at a concentration of 0.1 to 20% by weight.

13. The method of claim 12, wherein the cobalt precursor is $Co(NH_3)_6Cl_3$, or contains a cobalt complex ion obtained by treating at least one cobalt compound selected from the group consisting of $Co(NO_3)_2$, $CoCl_2$, and $Co(acac)_3$ with ammonia water, followed by filtration.

14. The method of claim 1, wherein the pH-adjusted aqueous solution of the cobalt precursor and the pH-adjusted aqueous dispersion of the pretreated silica in step e) are mixed at a ratio such that the amount of the cobalt precursor is at least 1% by weight, based on the pretreated silica.

15. The method of claim 1, wherein the thermal treatment in step g) is conducted in an oxygen-containing atmosphere at 250 to 1000° C.

16. The method of claim 1, wherein the catalyst has cobalt at a content of at least 1% by weight.

17. The method of claim 1, wherein the catalyst is substantially free of alkali metals.

\* \* \* \* \*